(12) United States Patent
Zhao

(10) Patent No.: US 7,513,903 B1
(45) Date of Patent: *Apr. 7, 2009

(54) ORGAN CULTURE IN SITU

(76) Inventor: Iris Ginron Zhao, C/O Michael R. Doram, 1028 N. Lake Ave., Suite #202, Pasadena, CA (US) 91104

( * ) Notice: Subject to any disclaimer, the term of this patent is extended or adjusted under 35 U.S.C. 154(b) by 677 days.

This patent is subject to a terminal disclaimer.

(21) Appl. No.: 10/841,717

(22) Filed: May 8, 2004

(51) Int. Cl.
*A61B 17/08* (2006.01)
*A61B 17/32* (2006.01)
*A61B 17/22* (2006.01)

(52) U.S. Cl. ............ 606/153; 424/569; 606/159; 606/167; 606/184

(58) Field of Classification Search ........ 606/159, 606/153, 167; 604/6.14; 424/569
See application file for complete search history.

(56) References Cited

U.S. PATENT DOCUMENTS

| | | | | | |
|---|---|---|---|---|---|
| 3,805,793 | A | * | 4/1974 | Wright | 604/22 |
| 4,818,291 | A | * | 4/1989 | Iwatsuki et al. | 106/124.1 |
| 5,389,096 | A | * | 2/1995 | Aita et al. | 606/15 |
| 5,522,815 | A | * | 6/1996 | Durgin et al. | 606/50 |
| 5,620,414 | A | * | 4/1997 | Campbell, Jr. | 604/22 |
| 5,633,002 | A | * | 5/1997 | Stricker et al. | 424/426 |
| 5,702,412 | A | * | 12/1997 | Popov et al. | 606/159 |
| 5,833,644 | A | * | 11/1998 | Zadno-Azizi et al. | 604/509 |
| 6,019,788 | A | * | 2/2000 | Butters et al. | 623/1.35 |
| 6,117,148 | A | * | 9/2000 | Ravo et al. | 606/153 |
| 6,152,141 | A | * | 11/2000 | Stevens et al. | 128/898 |
| 6,168,623 | B1 | * | 1/2001 | Fogarty et al. | 623/1.3 |
| 6,245,083 | B1 | * | 6/2001 | Black et al. | 606/153 |
| 6,248,933 | B1 | * | 6/2001 | Haber et al. | 800/18 |
| 6,579,311 | B1 | * | 6/2003 | Makower | 623/1.23 |
| 6,749,617 | B1 | * | 6/2004 | Palasis et al. | 606/181 |
| 6,824,549 | B1 | * | 11/2004 | Chao | 606/159 |
| 6,887,249 | B1 | * | 5/2005 | Houser et al. | 606/108 |

* cited by examiner

*Primary Examiner*—Leslie Deak
*Assistant Examiner*—Adam Marcetich

(57) ABSTRACT

A method of increasing blood supply to an ischemic area with a cultured vessel in situ, comprising: 1) selecting a narrow artery responsible to an ischemic area; 2) selecting a vein drawing blood from the ischemic area and can be spared from venous blood return, multiple venous lateral system, and volume conserving venous system; 3) making a hole or flap on opposite lateral walls and wall complex of the artery and vein; 4) connecting the artery and vein so that at least 20% by volume blood in the artery will be lead into the venous network while resistance adjustment remains but total resistance is reduced. The connection allows blood flow through the lumen created between two openings in the vein and artery, and comprises an extravascular wrapping configured to provide extravascular support and promote endothelial cell growth over the interior surface of the connection between vessels.

10 Claims, 1 Drawing Sheet

1a.
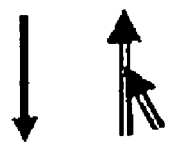
1b.
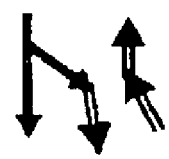
1c.
1d.

ORGAN CULTURE IN SITU

BACKGROUND OF THE INVENTION

1. Technical Field

The disclosure relates to a method and device for physiologically inducing blood supply to culture organ in situ.

2. Description of the Related Art

Vascular bypass surgery has been widely used to correct vessel stenosis, which is based on sutured anastomosis and availability of graft for substituting a narrowed artery. However, those skilled in the art are still currently confronted with particularly difficult problem cases. (US patent issued to Miyata et al. U.S. Pat. No. 4,098,571 for heterograft substitute blood vessel; to Chanda et al U.S. Pat. No. 5,645,587 for prevention of calcification and degeneration of implanted grafts; to Katsuen et al U.S. Pat. No. 5,691,203 for serum-free culture of human vascular endothelia cells; to Horiguchi U.S. Pat. No. 5,755,779 for blood stream adjuster, to Edelman et al U.S. Pat. No. 5,766,584 for inhibition of vascular smooth muscle cell proliferation with implanted matrix containing vascular endothelial cells; to Epstein et al U.S. Pat. No. 5,951,589 for expansile device for use in blood vessels; to Krajicek U.S. Pat. No. 5,968,089 for internal shield of a anastomosis; to Rateliff et al U.S. Pat. No. 5,968,090 for a endovascular graft and method; to Kranz U.S. Pat. No. 5,968,093 for a stent comprising at least one thin walled, tubular member). In particular, high vessel resistant cases speed up the narrowing process. Consequently, even with the use of stents, maximum permitted blood supply does not last long enough and bypass surgery may have to be done repeatedly.

It is difficult to suture vessels having a caliber or diameter smaller than 0.2-1 mm and a stent requires even bigger caliber to be inserted. Autografts are not always available and cultured heterograft vessels can cause rejection. It is thus a surprise to provide a blood flow as leading force for the vascular endothelium to grow as cultured in situ without suture, which breaks the lower limitation of vessel caliber requirement. In addition, full transfer of arterial pressure wave results in damage and intimal hyperplasia to the vein at the anastomosis and subsequent occlusion or thrombosis as in conventional bypass. The smaller the artery is and the less pressure and structure difference exists between the artery and vein, the better the outcome can be. The earlier the collateral bypass can be established, the longer the preventive effect can be achieved.

BRIEF DESCRIPTION OF DRAWING 1a. showing that before the procedure, the artery's blood flow and vein blood flow are separate.

1b. showing after applying this method, the result should be a blood flow from an artery (single black line) flowing into a vein network (double black lines)

1c. showing a naked blood flow.

1d. showing the long connective tube acting as an extravascular cuff/wrapping.

DETAILED DESCRIPTION OF THE INVENTION

To overcome the defects inherited from prior art, e.g., shortage of grafts, relapse after surgery, trauma of stent, size limitation for suture and stent, the application modifies bypass technique as close to physiology as possible and thus reduces recurrent risk. Since dynamic force of blood flow leads angiogenesis and neovascularization, suture is not necessary. As newly formed budding and sprouting from vessels need time to age, the chance of stenosis and obstruction of newly formed vessel are lowered. Plus, veins are usually spared from artery stenosis and hypertension, and therefore the disclosure provides a novel approach to further reduce stenosis. In addition, to solve hyperdisplasia, A-V aneurysm, and obstruction consequence following prior art, the disclosure divides only 20-70% blood flow from artery system into adjacent vein system, which reduces not only tissue ischemia caused by artery or arteriole obstruction but also reduces long-term vessel resistance, which contributes to hypertension and high relapse rate in conventional bypass surgery.

Upon dynamics review of blood flow in human, main blood pressure and vessel resistance are raised by small artery (>50µ), arterioles (50-20µ) and precapillary sphincter at metarteriole (10-15µ). In the fingers and palms, there are short channels that connect arterioles to venules, bypassing the capillaries. These arteriovenous (A-V) anastomoses, or shunts, have thick, muscular walls and are abundantly innervated, presumably by vasoconstrictor nerve fibers (William G. Ganong, Review of Medical Physiology, p 550-553, 1999). However, although the disclosure connects a small artery to a small vein also, it acts to increase capillary blood flow rather than to steal blood from lower reaches of supplied area. The vein under the A-V connection is opened to small artery so that the blood in the small artery will flow in increased cross-sectional channels whereas the vein at the connection is closed and therefore blood return above this point is the A-V connection is not sutured as in conventional anastomosis, instead, there is no trauma. Because of the volume reduction in the artery system, its blood flow after the bypass will confront at least 20% less resistance. The blood supply in the previous vein system should confront very little or no resistance. Since the total cross sectional area of venule is close to the sectional area of capillaries that is 10 times bigger than small arteries and arterioles, activating 10% by volume reserved venule system, by theory, would cover all small artery supplied area with physiologic function reserved in maximum. Of course the new growth vessel is supposed to be innervated by the nerve arose from the budding of small artery side and to inherit small artery characteristics like a young vessel does. Furthermore, since some precapillary sphincter has been bypassed, the resistance to ischemia tissue and blood pressure are reduced. Therefore, the risk of recurrent stenosis is greatly reduced and consequently long-term success after surgery is increased.

It is worth noticing how a vessel hemorrhage turns into a new vessel. Since neovascularization has been the last stage due to the cause of severe hypoxemia, microaneurysm is actually an attempt for more blood supply, where red blood cells come from the up side of the artery and exist on lower side depending on the pressure gradient created thereof. If the neck is too small for the two, single red blood cell will come and leave one by one in order to keep the circuit, which implies how the body struggles for every red blood cell to come through. Rather than sealing the neck of a microaneurysm, the application means to activate unused vein compensative system to subside insufficient artery supply. In reverse to reducing neovascularization, vascular endothelium growth is enhanced. Since endothelium has a growth peak about 3-7$^{th}$ day after a surgery, the release of neovascularization enhancers is designed to stop as soon as the endothelium has covered the blood flow. When a blood stream flows in a groove, channel, or artificial frame, vascular endothelial cells most likely grow and reach another blood stream successfully. After a bleeding continuously strikes on a point of another vessel's wall, the wall being stricken will open and accept the flow from the bleeding artery. Microaneurysms are formed when the bleeding whirls in loose tissue stria until exhausted at the center of the whirl. Under the condition of hypoxemia or stress, a blood stream may not clot as normal vessel does. Since accelerated formation of neovascularization usually occurs near wound borders, factors present in wound healing may enhance the formation of revascularization in susceptible tissue.

In summary, the invention is a method of using a bypass to physiologically induce blood supply and perfusion to an organ comprises a connection, wherein said connection comprising: a) a blood flow, b) a lumen or two openings on vessel walls, c) an extra-vascular glue, cuff, wrapping, or an attachable tube, which provides extra-vascular support as a vessel wall and enhances endothelial cells to line over the interior surface of the connection as cultured vessel in situ.

This connection is shaped as blood vessel, tissue groove, artificial graft, or a tube.

Above tube of cuff is made of scrum, absorbable glue, collagen, fibrin, gelatin, vascular endothelium component, vitreous body compound, polymer, arginine, glycine, protein, carbohydrate, polysaccharide, or a mixture.

Above removable punching device further providing an adjustable gas, vacuum or hook for controlling the debris motion from a punched vessel wall.

Above removable punching device further comprising a micropipette for delivering a chemical resolvent agent to erode an orifice on the lateral wall of a vessel to loose gap, bond, or junction of a vessel for easing endothelial cells to expand or and move.

Such connection providing a pressure gradient so that the direction of blood flow in the win will be constantly reversed.

Particularly, the mammal is a human who has vascular disorder or ischemia tissue, area, or organ. Since the use of such bypass was never recognized, the device and connection of the solution therefore are unobvious over prior record.

According to general human vessel data, the wall thickness of 30µ-lumen diameter arteries is about 20µ and the thickness of 30µ veins is only 3µ. It is desirable for the microsurgery device to create a small orifice, hole or flap in a range of equivalent of 10µ-1 mm caliber diameters in plane and 1-600µ in depth on the wall of small vein. The device should be a removable punch device. Therefore, after the device has completed the hole or flap or lumen, the blood flow can go through. For example, a laser, circular puncher, catheter, reversed deep ultraviolet wave, ultrasound, or their combination. The circular puncher is selected from needle or cornea circular puncher having its diameter reduced to approximately 10µ-1 mm. The catheter or probe can further inject a coaulatable fluid during its proceeding around the lumen, hole, or flap that has been made so that such fluid will form a solid wall or connection within 1 second to 20 minutes.

The operative end of the device comprises a tapered ending tip or micropipette having a central area or opening approximately 1-10µ. The energy source is selected from the group including laser, reversed deep ultraviolet wave, and ultrasound having energy sufficient to free gap and tight junction of cells to create a hole like opening on vessel wall. For example, cool lasers around 190-650 nm wavelength. Photosensitive marker may be added to increase the absorption of the vessel wall. Ideally, the laser wave should match the absorbable peak of the wall that needs a punched hole or flap. For the fine puncture and focus, an endoscopic or catheter puncher device is needed. A 193 nm argon excimer laser-like device is ideal to interact with vessel wall in a photochemical rather than a thermal mode so that most energy of the photon goes to free the gap, bond, and junction rather than heat the surrounding. Currently, "ArF excimer laser" has principal application in the field of refractive surgery to ablate layers of the cornea fibers for vision correction (Lewis et al.: Method & a device for cold laser microsurgery with highly localized tissue removal, U.S. Pat. No. 5,288,288, 1994) (Freeman et al., High resolution, high speed, programmable laser beam modulating apparatus for microsurgery, U.S. Pat. No. 5,624,437, 1997). Since the transparency of vessel wall is lower than cornea, the goal of the present microsurgery punching device is to free gap, bond, and junction of cells without thermal damage and to avoid abating layers of fibers. The advantage to do so is because to free one cell will free all surroundings and therefore a smooth hole can be created with least damage. When glue holds opposite walls of an artery and a vein next to each other, the orifice or pass on the lateral wall complex of such vessels is a mirror to each other. Preferably, the connection is absorbable and therefore, these two vessels can go back close to its original position. Hopefully, when the distance is increased, the endothelium growth will follow. By working cooperatively, the hole making device and the absorbable connection create a new bypass as an expected result.

When a laser microbeam or reversed ultraviolet is making a lateral opening through vessel walls, punctured debris is sucked into the device or forming a flap to prevent the debris dropped into vessels. The area of removed muscle layer is bigger than the hole to prevent hyperplasia and obstruction. Endothelium is cut as a circle or a flap. Cutaneous catheter can be introduced for puncturing a hole from distance. Chemical resolvent and gap opener, e.g., trypsin, collagenase, EDTA, heparin, erosive acid, lipolysis agent, or a hypertonic solution, loose junction/gap and reduces the tension of expanding. An expandable device with resolvent enzyme can ease the expanding of new channel.

Differentiated from prior endovascular stent, this connection offers an absorbable extravascular cuff to support the blood stream and endothelium growth, which, of course, should not injure the endothelium as endovascular stent does, instead, it offers an interior surface for endothelial cells to line over to form a new vessel. This connection can be extremely short or quite long. Eventually the connection provides a cultured new vessel graft in situs that does not need suture. When a small artery and vein are sharing same sheath, the connection can directly be a blood flow. An attachable connection means: 1) a vivid blood stream, 2) a lumen, a pass or two holes for such blood stream to flow, and 3) an extra vascular glue or an attachable tube, a tissue cuff, wrap, channel, or graft with a kinking to hold its position, or only a groove of tissue stria, which resides the blood flow. The method includes: 1) put or wrap a glue on each wall of small artery and vein; 2) press these two vessels together so that the distance between these two vessels is reduced; 3) punch a hole on the opposite side of each lateral wall of these two vessels; 4) stick these two holes together to form a lumen; or 5) connect these two holes by attachable connective tube, which is a temporary vessel with endothelium adhesion capacity in its interior surface and glue feature outside to seal leakages.

The connection matrix can start as a coagulatable fluid. It should have 2 phases for flowing to the designed position, and thereafter coagulating to form a connection. The matrix is made of serum, collagen, gelatin, fibrin, fibronectin, carbohydrate, protein, connective tissue, glue, polymer, synthesis compound, or their mixture. The connection can be further mixed, coated with, or being capable of releasing a pharmaceutical effective amount of anti-coagulation agent, endothelium adhesive and growth factor, and angiogenesis agent. For example, heparin, degraded heparin, endothelial cell component, adenosine, arginine, glycine, viagra, viagra-like agent, chitosin, anti-coagulation agent, re-stenosis inhibitor, vascular endothelium growth factor, epithelium growth hormone, acidic and basic fibroblast growth factor, transforming growth factors α and β, tissue factor, factor V, angiogenin, platelet derived endothelial cell growth factor, IL 8, or an herb or compound which will enhance endothelium adhesion and growth, increase the number of circulating endothelium precursor, or increase blood circulation. Absorbable glue is used to reduce the distance between a small artery and vein and hold the relative position of these two vessels like "> <" so that a laser needle can punch a hole (lumen) at the site where artery and vein are facing each other laterally.

Applicants prefer the vessels appearing on the surface of ischemia tissue or organ, e.g., coronary vessels on the heart. The vessels can also be on eye, brain, lung, spine, pancreas, gastrointestine, or a membrane, preferably the vessels can be seen directly.

Because sleep helps wound recovering, rejuvenation, and normalizing cortisol level, the method further comprises a step of providing a therapeutic effective amount of an anxiolytic drug or a hypnotic drug being capable of inducing or prolonging a sleep-like period, e.g. sodium thiopental, chlorpromazine, chloral hydrate, diazepam, clonazepam, essential amino acid, valium, or combinations thereof. Sodium thiopental is preferred due to its inducing immediate sleep, making people feel like a normal sleep.

While the whole disclosure has been described with respect to limited number of embodiments, it will be appreciated that many variations, modifications and other applications of the inventions may be made. It is therefore intended that such changes and modifications be covered by the claims appended hereto.

What is claimed is:

1. A method of reducing mammal vessel resistance and increasing blood supply and perfusion to an ischemia tissue, area, or organ with a cultured vessel in situ, comprising:
    selecting a narrow artery or arteriole which is responsible to a local ischemia tissue, area, or organ,
    selecting a vein or venule that is capable of drawing blood from said ischemia area and can be spared from vein blood return, multiple vein lateral system, or volume conserve vein system,
    using a microsurgery device to make a hole or a flap on opposite lateral walls or wall complex of said artery or arteriole and said vein or venule, wherein said hole or flap having equivalent dimensions of approximately 10 microns-1 mm in plane and 1-600 microns in depth,
    connecting the artery or arteriole to the vein or venule so that at least 20% by volume blood in the artery or arteriole will be lead into the vein network while resistance adjustment of the vessel is remained but total resistance is reduced,
    wherein said connection is configured to allow blood flow through the lumen created between two openings in said vein or venule and artery or arteriole, and wherein said connection comprises an extravascular wrapping configured to provide extravascular support and promote endothelial cell growth over the interior surface of the connection between vessels,
    wherein the process is performed on cultured vessels in situ.

2. The method of claim 1 wherein said microsurgery device is a removable punch device comprising a laser, circular puncher, reversed deep ultraviolet wave, ultrasound, or a combination thereof.

3. The method of claim 1 further comprising:
    providing a tapered micropipette or tip having a diameter approximately 10 microns-1 min with respect to said vessel wall for making a hole, a circle, or a flap having equivalent dimensions of approximately 10 microns-1 mm in plane and 1-600 microns in depth, and
    delivering a focused energy or resolvent agent through said pipette or tip in an amount sufficient to free or break down gap, bond, or junction of cells on a selected part of vessel wall to form a permanent blood pass from a small artery to a small vein.

4. The method of claim 1 wherein said microsurgery device comprising a micropipette for delivering a chemical resolvent agent to erode an orifice on the lateral wall of a vessel, or easing endothelial cells to expand and move.

5. The method of claim 1 further comprising a step of providing an adjustable gas for controlling debris motion from a punched vessel wall.

6. The method of claim 1 further comprising a step of injecting a coagulatable fluid around the lumen, hole, or flap that has been made so that said fluid will form a solid vessel-like wall or connection within 20 minutes.

7. The method of claim 1 wherein said connection is shaped as a blood vessel, tissue groove, artificial graft or tube.

8. The method of claim 1 wherein said connection comprises serum, vitreous body component, or a mixture thereof.

9. The method of claim 1 wherein said connection comprises a pharmaceutically effective amount of anti-coagulation agent, endothelium adhesion enhancer or blood circulation increaser.

10. The method of claim 1 further comprising a step of providing a sedative, anxiolytic, or hypnotic drug in an amount effective for enhancing convalescence.

* * * * *